United States Patent [19]
Katz

[11] Patent Number: 5,952,384
[45] Date of Patent: *Sep. 14, 1999

[54] METHOD AND COMPOSITION FOR TREATING MAMMALIAN DISEASES CAUSED BY INFLAMMATORY RESPONSE

[75] Inventor: Stanley E. Katz, Milltown, N.J.

[73] Assignee: Cellular Sciences, Inc., Flemington, N.J.

[ * ] Notice: This patent is subject to a terminal disclaimer.

[21] Appl. No.: 09/040,678

[22] Filed: Mar. 18, 1998

Related U.S. Application Data

[62] Division of application No. 08/709,043, Sep. 6, 1996, Pat. No. 5,798,388
[60] Provisional application No. 60/003,962, Sep. 19, 1995.
[51] Int. Cl.[6] .......................... A61K 31/19; A61K 31/22
[52] U.S. Cl. .................. 514/625; 514/909; 514/557; 514/826; 514/558; 514/559; 514/560
[58] Field of Search ..................................... 514/625, 909, 514/557, 826, 558, 559, 560

[56] References Cited

U.S. PATENT DOCUMENTS 5,256,697 10/1993 Miller et al. .............................. 514/625
5,686,089 11/1997 Mitra et al. .............................. 424/405

OTHER PUBLICATIONS

Database Chemical Abstracts on STN, Orlowska et al, AN Jan. 1972:538064.

*Primary Examiner*—Keith D. MacMillan
*Attorney, Agent, or Firm*—Richard R. Muccino

[57] ABSTRACT

A method for treating the disease state in mammals caused by mammalian cells involved in the inflammatory response is disclosed. Mammalian cells participating in the inflammatory response are contacted with an inflammatory response mediator which reduces the undesired inflammatory response and is an antioxidant. The inflammatory response mediator may further provide a cellular energy source and be a building block in the cellular synthesis of other cellular components. Composition, for reducing and treating undesired inflammatory response are also disclosed.

11 Claims, No Drawings

METHOD AND COMPOSITION FOR TREATING MAMMALIAN DISEASES CAUSED BY INFLAMMATORY RESPONSE

This application claims benefit of Provisional application 60/003,962 filed Sep. 19, 1995.

This is a divisional application of patent application Ser. No. 08/709,043, U.S. Pat. No. 5,798,388 filed 6 Sep. 1996.

BACKGROUND OF THE INVENTION

1. Field of the Invention

This invention pertains to therapeutic methods of preventing and treating the damage and resulting disease state in mammals caused by mammalian cells involved in the inflammatory response resulting in undesired respiratory bursting, production of enzymes and cellular signaling agents in mammalian cells. This invention also pertains to compositions used in the therapeutic methods.

2. Description of the Prior Art

Reactive oxygen species are generated by cells in response to inter alia aerobic metabolism, catabolism of drugs, toxins and other xenobiotics, ultraviolet and x-ray radiation and the respiratory burst of phagocytic cells (such as white blood cells) to kill invading bacteria and in response to foreign bodies. Hydrogen peroxide, for example, is produced during respiration of most living organisms especially by stressed and living cells.

These active oxygen species can injure cells. An important example of such damage is lipid peroxidation which involves the oxidative degradation of unsaturated lipids. Lipid peroxidation is highly detrimental to membrane structure and function and can cause numerous cytopathological effects. Cells defend against lipid peroxidation by producing radical scavengers such as superoxide dismutase, catalase, and peroxidase. Injured cells have a decreased ability to produce radical scavengers. Excess hydrogen peroxide can react with DNA to cause backbone breakage, produce mutations, and alter and liberate bases. Hydrogen peroxide can also react with pyrimidines to open the 5, 6-double bond. This reaction inhibits the ability of pyrimidines to hydrogen bond to complementary bases, Hallaender et al. (1971). Such oxidative biochemical injury can result in the loss of cellular membrane integrity, reduced enzyme activity, changes in transport kinetics, changes in membrane lipid content, and leakage of potassium ions, amino acids, and other cellular material.

The production of reactive oxygen intermediates has been suggested to cause many skin, tissue, and organ disorders such as atherosclerosis, arthritis, cytotoxicity, skin inflammation, photoaging, wrinkling, actinic keratosis, tumor formation, cancer, hypertension, Parkinson's disease, lung disease, and heart disease. The role of active oxygen radicals in promoting tumors has been proposed based on the findings that (a) tumor promoters increase the level of oxygen radicals, (b) many free radical generating systems promote tumors, and (c) certain antioxidants inhibit the biochemical effects of tumor promoters.

In Vitro, reactive oxygen intermediates can be generated in cellular culture media by autooxidation and photooxidation of media components. During excision and storage, transplant organs can suffer oxidative injuries which result in the loss of cellular membrane integrity and shorten the usable life of the organ.

When cells are stressed by oxidative injury, a resuscitation step is necessary to recondition the cells. Antioxidants have been shown to inhibit damage associated with active oxygen species. For example, pyruvate and other alpha-ketoacids have been reported to react rapidly and stoichiometrically with hydrogen peroxide to protect cells from cytolytic effects, O'Donnell-Tormey et al., *J. Exp. Med.,* 165, pp. 500–514 (1987).

U.S. Pat. No. 5,210,098 issued to Nath discloses a method to arrest or prevent acute kidney failure by administration of a non-toxic pyruvate salt to a patient in need of such treatment.

The Nath invention provides a therapeutic method comprising administration of an amount of pyruvate salt to a patient experiencing, or in danger of, acute renal failure. The pyruvate salt, preferably sodium pyruvate, is preferably dispersed or dissolved in a pharmaceutically acceptable liquid carrier and administered parenterally in an amount effective to arrest or prevent said acute renal failure, thus permitting restoration of normal kidney function. In some cases, the pyruvate may be infused directed into the kidney or into the proximal renal arterial circulation. The method is effective to prevent or counteract acute kidney failure due to a wide variety of causes, including, but not limited to, traumatic injury, including burn injury and obstruction; reperfusion following ischemia, inflammatory glomerulonephritis, and sepsis, e.g. due to gram negative bacterial infection.

Martin et al., 1994, U.S. Pat. No. 5,296,370, discloses therapeutic compositions for preventing and reducing injury to mammalian cells and increasing the resuscitation rate of injured mammalian cells. In one embodiment, the therapeutic composition comprises (a) pyruvate selected from the group consisting of pyruvic acid, pharmaceutically acceptable salts of pyruvic acid, and mixtures thereof, (b) an antioxidant, and (c) a mixture of saturated and unsaturated fatty acids wherein the fatty acids are those fatty acids required for the resuscitation of injured mammalian cells.

U.S. Pat. No. 5,256,697 issued to Miller et al., discloses a method for orally administering a therapeutically effective amount of a pyruvate precursor to a mammal to improve insulin resistance, lower lasting insulin levels and reduce fat gain.

U.S. Pat. Nos. 3,920,835, 3,984,556, and 3,988,470, all issued to Van Scott et al. disclose methods for treating acne, dandruff, and palmar keratosis, respectively, which consist of applying to the affected area a topical composition comprising from about 1% to about 20% of a lower aliphatic compound containing from two to six carbon atoms selected from the group consisting of alpha-hydroxyacids, alpha-ketoacids and esters thereof, and 3-hydroxybutryic acid in a pharmaceutically acceptable carrier. The aliphatic compounds include pyruvic acid and lactic acid.

U.S. Pat. Nos. 4,105,783 and 4,197,316, both issued to Yu et al., disclose a method and composition, respectively, for treating dry skin which consists of applying to the affected area a topical composition comprising from about 1% to about 20% of a compound selected from the group consisting of amides and ammonium salts of alpha-hydroxyacids, beta-hydroxyacids, and alpha-ketoacids in a pharmaceutically acceptable carrier. The compounds include the amides and ammonium salts of pyruvic acid and lactic acid.

U.S. Pat. No. 4,234,599, issued to Van Scott et al., discloses a method for treating actinic and nonactinic skin keratoses which consists of applying to the affected area a topical composition comprising an effective amount of a compound selected from the group consisting of alpha-hydroxyacids, beta-hydroxyacids, and alpha-ketoacids in a pharmaceutically acceptable carrier. The acidic compounds include pyruvic acid and lactic acid.

U.S. Pat. No. 4,294,852, issued to Wildnauer et al., discloses a composition for treating skin which comprises the alpha-hydroxyacids, beta-hydroxyacids, and alpha-ketoacids disclosed above by Van Scott et al., in combination with C3–C8 aliphatic alcohols.

U.S. Pat. No. 4,663,166, issued to Veech, discloses an electrolyte solution which comprises a mixture of L-lactate and pyruvate in a ratio from 20:1 to 1:1, respectively, or a mixture of D-beta-hydroxybutyrate and acetoacetate, in a ratio from 6:1 to 0.5:1, respectively.

Sodium pyruvate has been reported to reduce the number of erosions, ulcers, and hemorrhages on the gastric mucosa in guinea pigs and rats caused by acetylsalicylic acid. The analgesic and antipyretic properties of acetylsalicylic acid were not impaired by sodium pyruvate, Puschmann, *Arzneimittelforschung,* 33, pp. 410–415 and 415–416 (1983).

Pyruvate has been reported to exert a positive inotropic effect in stunned myocardium, which is a prolonged ventricular dysfunction following brief periods of coronary artery occlusions which does not produce irreversible damage, Mentzer et al., *Ann. Surg.,* 209, pp. 629–633 (1989).

Pyruvate has been reported to produce a relative stabilization of left ventricular pressure and work parameter and to reduce the size of infarctions. Pyruvate improves resumption of spontaneous beating of the heart and restoration of normal rates and pressure development, Bunger et al., *J. Mol. Cell. Cardiol.,* 18, pp. 423–438 (1986), Mochizuki et at., *J. Physiol. (Paris),* 76, pp. 805–812 (1980), Regitz et at., *Cardiovasc, Res.,* 15, pp. 652–658 (1981), Giannelli et al., *Ann. Thorac. Surg.,* 21 pp. 386–396. (1976).

Sodium pyruvate has been reported to act as an antagonist to cyanide intoxication (presumably through the formation of cyanohydrin) and to protect against the lethal effects of sodium sulfide and to retard the onset and development of functional, morphological, and biochemical measures of acrylamide neuropathy of axons, Schwartz et al., *Toxicol. App. Pharmacol.,* 50 pp. 437–442 (1979), Sabri et al., *Brain Res.,* 483, pp. 1–11 (1989).

A chemotherapeutic cure of advanced L1210 leukemia has been reported using sodium pyruvate to restore abnormally deformed red blood cells to normal. The deformed red blood cells prevented adequate drug delivery to tumor cells, Cohen, *Cancer Chemother, Pharmacol.,* 5, pp. 175–179 (1981).

Primary cultures of heterotopic tracheal transplant exposed on in vivo to 7, 12-dimethylbenz(a)anthracene were reported to be successfully maintained in enrichment medium supplemented with sodium pyruvate along with cultures of interleukin-2 stimulated peripheral blood lymphocytes, and plasmacytomas and hybridomas, pig embryos, and human blastocysts, Shacter, *J. Immuno. Methods,* 99, pp. 259–270 (1987), Marchok et al., *Cancer Res.,* 37, pp 1811–1821 (1977), Davis, *J. Reprod. Fertil. Suppl.,* 33 pp. 115–124 (1985), Okamoto et al., *No To Shinkei,* 38, pp. 593–598 (1986), Cohen et al., *J. In Vitro Fert. Embryo Transfer,* 2, pp. 59–64 (1985).

U.S. Pat. Nos. 4,158,057, 4,351,835, 4,415,576, and 4,645,764, all issued to Stanko, disclose methods for preventing the accumulation of fat in the liver of a mammal due to the ingestion of alcohol, for controlling weight in a mammal, for inhibiting body fat while increasing protein concentration in a mammal, and for controlling the deposition of body fat in a living being, respectively. The methods comprise administering to the mammal a therapeutic mixture of pyruvate and dihydroxyacetone, and optionally riboflavin. U.S. Pat. No. 4,548,937, issued to Stanko, discloses a method for controlling the weight gain of a mammal which comprises administering to the mammal a therapeutically effective amount of pyruvate, and optionally riboflavin. U.S. Pat. No. 4,812,479, issued to Stanko, discloses a method for controlling the weight gain of a mammal which comprises administering to the mammal a therapeutically effective amount of dihydroxyacetone, and optionally riboflavin and pyruvate.

Rats fed a calcium-oxalate lithogenic diet including sodium pyruvate were reported to develop fewer urinary calculi (stones) than control rats not given sodium pyruvate, Ogawa et al., *Hinvokika Kivo,* 32, pp. 1341–1347 (1986).

U.S. Pat. No. 4,521,375, issued to Houlsby, discloses a method for sterilizing surfaces which come into contact with living tissue. The method comprises sterilizing the surface with aqueous hydrogen peroxide and then neutralizing the surface with pyruvic acid.

U.S. Pat. No. 4,416,982, issued to Tauda et al., discloses a method for decomposing hydrogen peroxide by reacting the hydrogen peroxide with a phenol or aniline derivative in the presence of peroxidase.

U.S. Pat. No. 4,696,917, issued to Lindstrom et al., discloses an irrigation solution which comprises Eagle's Minimum Essential Medium with Earle's salts, chondroitin sulfate, a buffer solution, 2-mercaptoethanol, and a pyruvate. The irrigation solution may optionally contain ascorbic acid and alpha-tocopherol. U.S. Pat. No. 4,725,586, issued to Lindstrom et al., discloses an irrigation solution which comprises a balanced salt solution, chondroitin sulfate, a buffer solution, 2-mercaptoethanol, sodium bicarbonate or dextrose, a pyruvate, a sodium phosphate buffer system, and cystine. The irrigation solution may optionally contain ascorbic acid and gamma-tocopherol.

U.S. Pat. No. 4,847,069, issued to Bissett et al., discloses a photoprotective composition comprising (a) a sorbohydroxamic acid, (b) an antiflammatory agent selected from steroidal anti-inflammatory agents and a natural anti-inflammatory agent, and (c) a topical carrier. Fatty acids may be present as an emollient. U.S. Pat. No. 4,847,071, issued to Bissett et al., discloses a photoprotective composition comprising (a) a tocopherol or tocopherol ester radical scavenger, (b) an anti-inflammatory agent selected from steroidal anti-inflammatory agents and a natural anti-inflammatory agent, and (c) a topical carrier. U.S. Pat. No. 4,847,072, issued to Bissett et al. discloses a topical composition comprising not more than 25% tocopherol sorbate in a topical carrier.

The addition of sodium pyruvate to bacterial and yeast systems has been reported to inhibit hydrogen peroxide production, enhance growth, and protect the systems against the toxicity of reactive oxygen intermediates. The optimum ratio of unsaturated to saturated fatty acids contained within chicken fat enhanced membrane repair and reduced cytotoxicity. The antioxidants glutathione and thioglycollate reduced the injury induced by oxygen radical species, Martin, Ph.D. thesis, (1987–89).

While the above therapeutic compositions and methods are reported to inhibit the production of reactive oxygen intermediates, none of the compositions and methods treats the damage and resulting disease state in mammals caused by undesired respiratory bursting, production of enzymes and cellular signaling agents in mammalian cells.

SUMMARY OF THE INVENTION

The present invention pertains to a method for treating the disease state in mammals caused by mammalian cells involved in the inflammatory response and compositions useful in the method. The method for treating the disease state in mammals caused by mammalian cells involved in the inflammatory response comprises: contacting the mammalian cells participating in the inflammatory response with an inflammatory mediator; wherein the inflammatory mediator is present in an amount capable of reducing the undesired inflammatory response and is an antioxidant.

The inflammatory mediator in addition to reducing the undesired inflammatory response and being an antioxidant, may further provide a cellular energy source and be a building block in the cellular synthesis of other cellular components. The inflammatory mediator may also increase cellular metabolic rate.

The present invention also pertains to compositions for reducing and treating the disease state in mammals caused by undesired inflammatory response comprising: An inflammatory response mediator; and a carrier composition; wherein the inflammatory response mediator is an antioxidant and capable of reducing undesired inflammatory response in mammalian cells.

The inflammatory response mediators may be used individually, in combination and further in combination with a therapeutic agent such as an antibacterial, antiviral, antifungal, protein, enzyme, anithistamine, hormone, nonsteroidal antiinflammatory, cytokine, and steroid.

A preferred method of administering the inflammatory mediator is by inhalation.

DETAILED DESCRIPTION OF THE INVENTION

Therepeutic compositions and a method for treating the disease state in mammals caused by mammalian cells involved in the inflammatory response have been discovered. The mammalian cells primarily responsible for the inflammatory response are white blood cells or leucocytes.

In a method for treating the disease state in mammals caused by mammalian cells involved in the inflammatory response, mammalian cells are contacted with an inflammatory mediator. The inflammatory mediator is present in an amount capable of reducing the undesired inflammatory response and is an antioxidant.

The inflammatory response, often referred to as respiratory bursting, is the response of defensive mammalian cells primarily white blood cells or leucocytes. These cells normally respond to an injury or invasion of the mammal by releasing a number of active compounds at the injury or invasion site. Among the compounds released are enzymes such as proteases and active oxygen species such as hydrogen peroxide.

A purpose of the respiratory burst is to provide a battery of oxidizing agents in response to a stimulant that can be used by the leucocytes for the destruction of foreign cells, viruses, particulates and some toxins which have been ingested by or are in the vicinity of the leucocyte. The term "respiratory burst" refers to a coordinated series of metabolic events that take place when leucocytes are exposed to appropriate stimuli. This group of events underlies all oxygen dependent killings by leucocytes.

The first of these events is the sharp increase in oxygen uptake that occurs upon stimulation of the leucocytes. While oxygen consumption by resting leucocytes varies widely by cell type, all respond to appropriate stimuli with an increase in oxygen uptake.

Stimulation of the leucocyte also causes an increase in glucose oxidation via the hexose monophosphate shunt. The hexose monophosphate shunt is a metabolic pathway in which glucose is oxidized to carbon dioxide and a five carbon sugar, with NADP+ serving as electron aceptor. Activation of the hexose monophosphate shunt therefore means that the oxidation of NADPH to NADP+ increases during the respiratory burst.

The respiratory burst produces superoxide and hydrogen peroxide. Oxygen taken up by the respiratory burst is converted to superoxide. Hydrogen peroxide appears to arise during the respitarory burst mainly from the dismutation of superoxide anion.

$$O_2^- + O_2^- + 2H^+ \rightarrow H_2O_2 + O_2$$

It has been demonstrated by Root and Metcalf and reported in *J. Clin. Invest.* 60:1266 that 80 pcercent of the superoxide is converted to hydrogen peroxide, and this dismutation reaction is the only important source of the hydrogen peroxide generated during the burst. Hydrogen peroxide and superoxide are believed to be responsible for the killing by leucocytes.

Many agents, both soluble and particulate, are able to activate the respiratory burst. Particulate activating agents include bacteria, viruses and fungi for internal body organs or areas and bacteria, viruses, fungi, fibers, smoke, dust, ash, pollen, smog and the like for body cavities and organs such as the lungs, skin, digestive and excretory tracks open to the environment. Soluble agents can be toxins, medicinal compounds and soluble excretions of bacteria, fungi and infected mammalian cells and the like.

Activation of the respiratory burst in leucocytes usually follows exposure to the stimulus for less than a minute. Upon stimulation of the respiratory burst, the consumption of oxygen in leucocytes increases by over 100 fold resulting in, among other things, the production of superoxide, peroxide and hydrogen peroxide. The term "leucocytes" as used herein includes lymphocytes, phagocytes, macrophages and auxiliary cells.

Usually, after respiratory bursting the stimulent and/or the mechanism of stimulation turns off allowing the leucocyte to return to its normal resting state. When the bursting does not turn off, the inflammatory action of the leucocytes continutes unchecked causing a number of disease states. These disease states occur as the compounds produced by the leucocytes attack, injure and kill tissue cells and other leucocytes. It is this failure to turn off the respiratory burst and the resulting injury to surrounding tissue cells, blood cells, other leucocytes and injured cells that produces the disease states treated by the present invention. Undesired inflammatory response occurs when the inflammatory response causes injury to host cells and this injury poses an independent threat to the host.

In a preferred embodiment, the therapeutic compositions containing an inflammatory mediator are administered locally to the site of inflammation. In another preferred embodiment, the therapeutic compositions are administered systemically. In yet another preferred embodiment, the therapeutic compositions are administered systemically and locally concomitantly.

In a preferred embodiment, the therapeutic compositions are administered by inhalation. The therapeutic compositions may be first nebulized by any suitable means. The therapeutic compositions may be in liquid or solid form with liquid droplets or particle size being small enough to facilitate access to lung tissue by inhalation.

In another preferred embodiment, a sterile solution of therapeutic agent is nebulized and inhaled by the patient. A therapeutically effective amount of inflammatory medication is inhaled. This may be accomplished in a single inhalation or by repeated inhalations over a period of time typically 1 to 30 minutes. Preferrably, inhalation will be complete in less than 20 minutes. Most preferably inhalation will be complete in less than 15 minutes.

The term "injured cell" as used herein means a cell which has some or all of the following: (a) injured membranes so that transport through the membranes is diminished and may result in one or more of the following, an increase in toxins and normal cellular wastes inside the cell and/or a decrease in nutrients and other components necessary for cellular repair inside the cell, (b) an increase in concentration of oxygen radicals inside the cell because of the decreased ability of the cell to produce antioxidants and enzymes, and (c) damaged DNA, RNA and ribosomes which must be repaired or replaced before normal cellular functions can be resumed.

Preferably the inflammatory mediator when brought into contact with a mammalian cell provides a cellular energy source and a building block in the cellular synthesis of other cellular components.

The inflammatory response being reduced is at least one of the following: oxygen radical production, peroxide production, cytokine and/or protease production, prostiglandin production, erythema, histamine and interlukin production and like responses known in the art as inflammatory responses.

The preferred inflammatory mediator is at least one compound selected from the group consisting of a pyruvate precursor, pyruvate, a lactate precursor and lactate. A precursor is a substance from which another substance is formed and in this text also includes salts.

Preferably the pyruvate is selected from the group consisting of pyruvic acid, lithium pyruvate, sodium pyruvate, potassium pyruvate, magnesium pyruvate, calcium pyruvate, zinc pyruvate, manganese pyruvate, and the like and mixtures thereof. Sodium pyruvate is most preferred.

Another preferred inflammatory mediator is selected from the group consisting of pyruvyl-glycene, pyruvyl-alanine, pyruvyl-leucine, pyruvyl-valine, pyruvyl-isoleucine, pyruvyl-phenylalanine, pyruvamide, dihydroxyacetone, and propylene glycol.

Preferred salts of the inflammation mediator are salts that do not produce an adverse effect on the mammalian cell when applied as a salt of the inflammation mediator. Typical salts would be the lithium, sodium, potassium, aluminum, magnesium, calcium, zinc, manganese, ammonium and the like and mixtures thereof.

The lactate precursor is preferably selected from the group consisting of lactyl-glycene, lactyl-alanine, lactyl-leucine, lactyl-valine, lactyl-isoleuccine, lactyl-phenylalanine, lactamide and the various salts of lactate.

Compositions for reducing and treating the disease state in mammals caused by undesired inflammatory response comprise:

an inflammatory response mediator; and a carrier composition.

The carrier composition is selected from the group consisting of tablets, capsules, liquids, isotonic liquids, isotonic media, enteric tablets and capsules, parenterals, topicals, creams, gels, ointments, chewing gums, confections and the like.

The inflammatory mediator is administered in a therapeutically effective amount to reduce the undesired inflammatory response. Preferably from 0.001 to 10 grams per dose. More preferably 0.001 to 1 gram per dose and most preferably 0.001 to 0.25 grams per dose. It is understood that the method of administration and the condition being treated will greatly affect the dose required to achieve the therapeutic effect.

Typical airway diseases treatable by the present compositions and method include but are not limited to bronchial asthma, acute bronchitis, emphysema, chronic obstructive emphysema, centrilobular emphysema, panacinar emphysema, chronic obstructive bronchitus, reactive airway disease, cystic fibrosis, bronchiectasis, acquired bronchiectasis, kartaagener's syndrome, acelectasis, actue atelectasis, chronic acelectasis, pneumonia, essential thrombocytemia, legionnaires disease, psittacosis, fibrogenic dust disease, diseases due to organic dust, diseases due to irritant gases and chemicals, hypersensitivity diseases of the lung, idiopathic infiltrative diseases of the lungs and the like.

Particucular disease states to be treated are emphysema and asthma.

The inflammatory mediator of the present invention may be administered prior to, after and/or with other therapeutic agents. Typical therapeutic agents are antibacterials, antivirals, antifungals, antihistamines, proteins, enzymes, hormones, nonsteroidal antiinflammatories, cytokines, steroids, and the like.

Obviously, numerous modifications and variations of the present invention are possible in the light of the above teachings and the invention is not limited to the example herein. It is therefore understood that within the scope of the appended claims, the invention may be practiced otherwise than as specifically described herein.

EXAMPLE

Subject: A 59 year old male suffering from emphysema and restrictive airway disease was treated as described below for three (3) months. Prior to treatment the subject had limited capacity to breathe, did not respond to any other treatment, was on oxygen daily, and could not function at work (was on sabbatical leave). After three (3) months treatment he showed marked improvement. In fact, dramatic results were observed within two (2) weeks.

Treatment: The treatment was conducted as follows:

Five (5) milliliters of five (5) millimolar sodium pyruvate solution is filter sterilized through a 0.2 micron filter. The sterile pyruvate solution is placed into a "Pulmo Aid" nebulizer manufactured by DeVilbiss Co., Somerset, Pa. 15501-0635. The sterile pyruvate solution is nebulized by the Pulmo Aid device fitted with a disposable nebulizer and inhaled by the patient. The patient inhales normally from the Pulmo Aid nebulizer until all of the solution has been nebulized and inhaled. This inhalation step typically takes about ten (10) to twenty (20) minutes.

The patient is treated with this inhalation therapy periodically. Initially, treatments are about four (4) times a day at about six (6) hour intervals. Treatments were reduced to three (3) times a day at about eight (8) hour intervals after 30 days of therapy. Treatments were further reduced to once a day 60 DAYS AFTER ONSET OF TREATMENT. After ninety (90) days treatments are three to five times a week.

The following data shows results of various lung capacity and lung function tests administered before treatment and two (2) months after treatment was commenced.

| Type of test | Before Treatment | After two Months Treatment |
| --- | --- | --- |
| SVC (slow vital capacity) | 63 | 83 |
| IC (inspiratory capacity) | 64 | 69 |
| ERV (expiratory reserve volume) | 62 | 110 |
| MVV (maximnum ventiatory volume) | 19 | 25 |
| DCO (diffusion of carbon monoxide MI/min/mm Hg) | 27 | 39 |
| DSB (diffusion single breath) | 42 | 52 |
| O SAT (oxygen saturation) | 91 | 95 |

Observation: Twenty to thirty minutes after initial treatment, tidal volume increases, wheezing stops and an increase in exercise tolerance is observed. Reliance on "Proventil" (Albuterol made by Schering) is reduced from 1600 mg per day to 400 mg per day within the first two (2) weeks of treatment. Use of oxygen was eliminated immediately when treatment started.

Conclusion: Treatment did the following:
(1) Improved lung function by 20%.
(2) Decreased some medication levels and ceased use of oxygen.
(3) Reactive airway disease is reduced to the point that routine use of inhalers is not needed.
(4) Increased exercise tolerance has been tested and certified as being close to that of a person without emphysema and restrictive airway disease. Subject has been able to return to full work schedule at previous job.
(5) No recurrence of decreased pulmonary functions.
(6) Mental attitude has greatly improved.

While the method for treating the disease state in mammalian cells involved in the inflammatory response herein described constitute preferred embodiments of this invention, it is to be understood that the invention is not limited to this precise form of method and that changes may be made therein without departing from the scope of the invention which is defined in the appended claims.

I claim:

1. A method for treating airway disease in mammals caused by mammalian cells involved in the inflammatory response comprising:
   contacting the mammalian cells with an inflammatory mediator;
   wherein the inflammatory mediator is selected from the group consisting of pyruvate and a pyruvate precursor and is present in an amount capable of reducing the undesired inflammatory response and is an antioxidant.

2. The method of claim 1 wherein the inflammatory response being reduced is at least one of the following: oxygen radical production, hydrogen peroxide production, cytokine and protease production, prostaglandin production, erythema, histamine and interleukin production.

3. The method of claim 1 wherein the pyruvate is selected from the group consisting of pyruvic acid, lithium pyruvate, sodium pyruvate, potassium pyruvate, magnesium pyruvate, calcium pyruvate, zinc pyruvate, manganese pyruvate, and mixtures thereof.

4. The method of claim 1 wherein the pyruvate precursor is selected from the group consisting of, pyruvyl-glycine, pyruvyl-alanine, pyruvyl-leucine, pyruvyl-valine, pyruvyl-isoleucine, pyruvyl-phenylalanine, pyruvamide, and salts of pyruvic acid.

5. The method of claim 1 wherein the airway disease is selected from the group comprising acute bronchitis, chronic obstructive emphysema, centrilobular emphysema, panacinar emphysema, chronic obstructive bronchitis, reactive airway disease, cystic fibrosis, bronchiectasis, acquired bronchiectasis, kartaagener's syndrome, atelectasis, acute atelectasis, chronic atelectasis, pneumonia, legionnaires disease, psittacosis, fibrogenic dust disease, diseases due to organic dust, diseases due to irritant gases and chemicals, hypersensitivity diseases of the lung, idiopathic infiltrative diseases of the lungs and the like.

6. The method of claim 1 further comprising contacting the mammalian cells with a therapeutic agent.

7. The method of claim 6 wherein the therapeutic agent is administered prior to the inflammatory mediator.

8. The method of claim 6 wherein the therapeutic agent is administered concomitantly with administration of the inflammatory mediator.

9. The method of claim 6 wherein the therapeutic agent is administered after administration of the inflammatory mediator.

10. The method of claim 1 wherein the mammalian cells are white blood cells.

11. The method of claim 6 wherein the therapeutic agent is one or more agents selected from the group consisting of antibacterials, antivirals, antifungals, antihistamines, proteins, enzymes, hormones, nonsteroidal anti-inflammatories, cytokines, and steroids.

* * * * *